United States Patent
Tat et al.

(10) Patent No.: US 10,502,719 B2
(45) Date of Patent: Dec. 10, 2019

(54) ANALYSIS OF A STRUCTURE MODELED WITH INCONSISTENCIES MAPPED THEREON

(71) Applicant: THE BOEING COMPANY, Huntington Beach, CA (US)

(72) Inventors: Hong Hue Tat, Redmond, WA (US); Kelly M. Greene, Kent, WA (US); John Z. Lin, Renton, WA (US); Carlyn R. Brewer, Newcastle, WA (US); Russell Lee Keller, Maple Valley, WA (US)

(73) Assignee: The Boeing Company, Chicago, IL (US)

( * ) Notice: Subject to any disclaimer, the term of this patent is extended or adjusted under 35 U.S.C. 154(b) by 1005 days.

(21) Appl. No.: 14/832,575

(22) Filed: Aug. 21, 2015

(65) Prior Publication Data

US 2017/0052152 A1    Feb. 23, 2017

(51) Int. Cl.
*G01N 29/44* (2006.01)
*G06F 17/50* (2006.01)
*G01N 29/04* (2006.01)

(52) U.S. Cl.
CPC .............. *G01N 29/44* (2013.01); *G01N 29/04* (2013.01); *G06F 17/5018* (2013.01);
(Continued)

(58) Field of Classification Search
CPC ............... G06F 17/5018; G06F 3/1454; G06F 2217/16; G01N 3/00; G01N 29/44;
(Continued)

(56) References Cited

U.S. PATENT DOCUMENTS

2008/0183402 A1*  7/2008  Malkin ............... G06F 17/5018
                                                                 702/34
2009/0000382 A1    1/2009  Sathish et al.
(Continued)

FOREIGN PATENT DOCUMENTS

CN           102607935 B      1/2014

OTHER PUBLICATIONS

International Search Report dated Jan. 25, 2017 for Application No. 16173020.5.
(Continued)

*Primary Examiner* — Regis J Betsch
*Assistant Examiner* — Kaleria Knox
(74) *Attorney, Agent, or Firm* — Womble Bond Dickinson (US) LLP

(57) ABSTRACT

A method for analyzing a structure includes processing nondestructive inspection (NDI) data for a multi-layer structure to define areas of inconsistency at an internal layer or an interface between adjacent layers. The method includes mapping the areas of inconsistency to finite elements of a finite element model of a nominal of the structure. These finite elements are thereby identified as affected finite elements and include finite elements for the affected internal layer or interface. The method includes producing a reconstructed finite element model of the affected structure from the nominal finite element model, and a modified property or state value assigned to respective element datasets of the affected finite elements. The method includes performing a finite element method (FEM) failure analysis of the reconstructed finite element model under a load, which indicates an extent of residual integrity of the affected structure.

18 Claims, 7 Drawing Sheets

(52) U.S. Cl.
  CPC ............... *G01N 2291/011* (2013.01); *G01N 2291/2694* (2013.01); *G06F 2217/16* (2013.01); *G06F 2217/42* (2013.01); *G06F 2217/44* (2013.01)

(58) Field of Classification Search
  CPC ............ G01N 29/04; G01N 2291/011; G01N 2291/2694; G01S 15/899; G01F 2217/44
  USPC ................................. 702/34; 703/2; 345/34
  See application file for complete search history.

(56) References Cited

U.S. PATENT DOCUMENTS

| | | |
|---|---|---|
| 2010/0250148 A1 | 9/2010 | Meredith et al. |
| 2014/0022281 A1* | 1/2014 | Georgeson ............ G06F 3/1454 345/633 |
| 2014/0278292 A1* | 9/2014 | Grellou ............... G06F 17/5018 703/2 |

OTHER PUBLICATIONS

L. Iannuci, "Dynamic Delamination Modelling Using Interface Elements", Computer and Structures, vol. 84, No. 15-16, Jun. 1, 2006, pp. 1029-1048.

William Henry Pfeifer, "Computer Tomography of Advanced Composite Materials", Advanced Composite Materials, 1985.

Qin Shen et al., "Ultrasonic NDE Techniques for Impact Damage inspection on CFRP Laminates", Journal of Materials Science Research, vol. 1, No. 1, Jan. 2012.

Ali Abdul-Aziz et al., "A CAD Approach to Integrating NDE With Finite Element," National Aeronautics and Space Administration, NASA/TM 2004-212904, Apr. 2004.

Ali Abdul-Aziz et al., "Nondestructive Evaluation Correlated With Finite Element Analysis," http://www.grc.nasa.gov/WWW/RT/RT1998/5000/5920aziz.html.

Robert S. Frankle, "Application of NDE Data to Finite Element Analysis of Parts Containing Defect," Damage Detection in Composite Materials, ASTM STP Issue 1128, John E. Masters, Ed., American Society for Testing and Materials, Philadelphia, 1992, pp. 85-100.

Giannis et al., "Maximising the Benefit of Non-Destructive Inspection Data to Evaluate the Damage Tolerance Performance of Composites", SAMPE Technical Conference Proceedings, Wichita, KS, Oct. 21-24, 2013, Society for the Advancement of Material and Process Engineering.

Tom Sharp, "Inspection Data Management", Aircraft Airworthiness and Sustainment Conference, Austin, Texas, 2010.

* cited by examiner

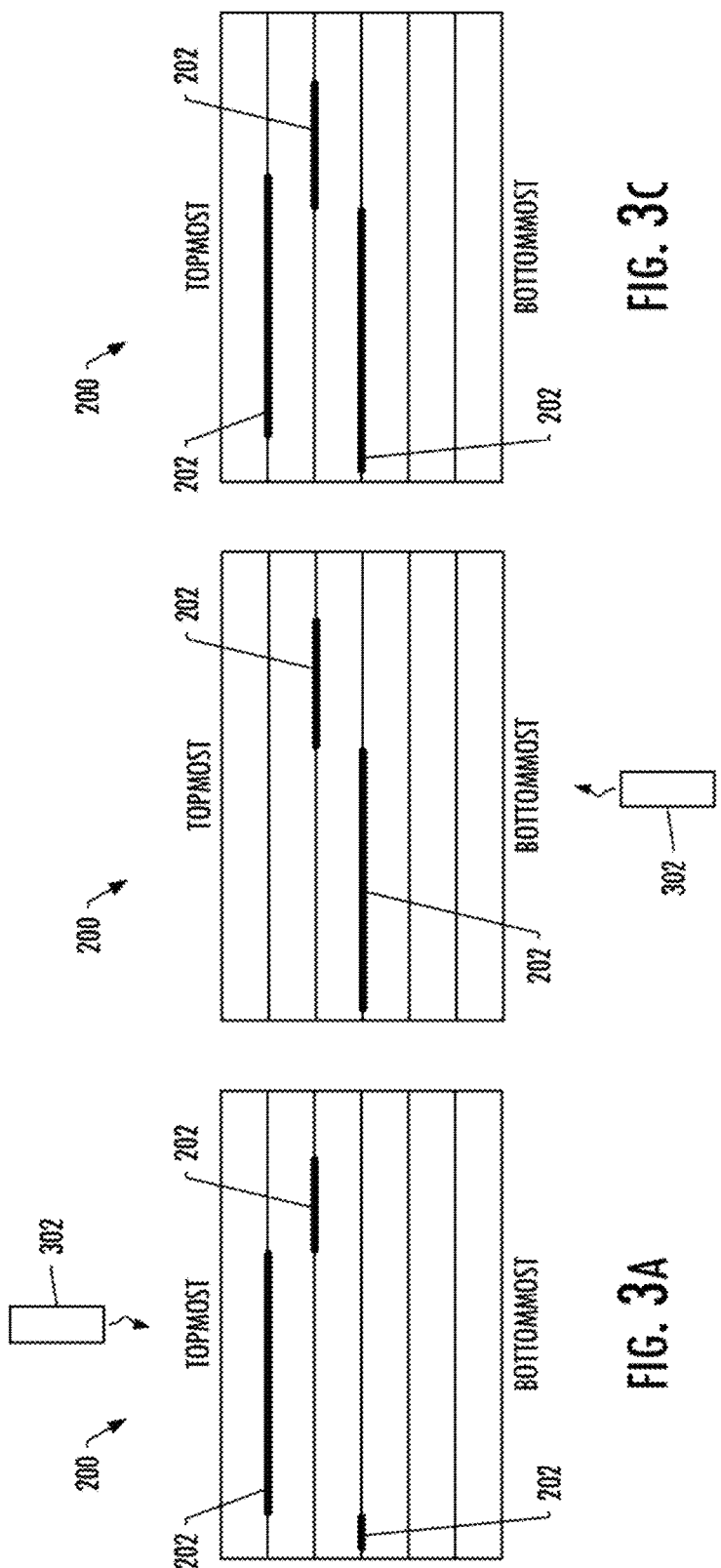

ANALYSIS OF A STRUCTURE MODELED WITH INCONSISTENCIES MAPPED THEREON

TECHNOLOGICAL FIELD

The present disclosure relates generally to analysis of a structure and, in particular, to progressive failure analysis of a structure modeled with inconsistencies.

BACKGROUND

The use of composite materials is increasingly becoming the new norm for airframe construction. Many composite aircraft structures are made of monolithic laminates that are susceptible to inconsistencies, such as defects or damage. These inconsistencies may occur on the factory floor for just-manufactured structures during an aircraft build, as well as in the field for in-service aircraft. This may be equally true of structures in a number of contexts, such as in the context of structures of any of a number of manned or unmanned vehicles (e.g., motor vehicles, railed vehicles, watercraft, aircraft, spacecraft).

Primary composite structures may be designed to a positive compression after impact (CAI) margin based on specific impact energy levels. In practice, however, impact events may be complicated and impact energy may be unknown. When an impact event occurs, nondestructive inspection (NDI) procedures may be performed to determine the extent of some damage to or defect in a structure. In the case of ultrasonic inspection, the NDI data in the form of C-Scan images may be available to service engineers who have to disposition such damage/defect according to preset allowable damage limits (ADLs) defined in a structural repair manual (SRM).

Current techniques for defect and damage analysis may also be applicable to other types of inconsistencies, such as impact-induced delamination, topology change, heat-induced chemical change and the like. These techniques are highly-conservative processes, from interpretation of the NDI data to the analysis of the defective/damaged structure. And these highly-conservative processes can potentially lead to unnecessary rework (e.g., repair, replacement). It may therefore be desirable to have an apparatus and method that addresses these challenges, and improves upon existing practices while still ensuring continued airworthiness per regulatory requirements.

BRIEF SUMMARY

Example implementations of the present disclosure are directed to an improved apparatus, method and computer-readable storage medium for analysis of a structure modeled with inconsistencies mapped thereon. In some example implementations, NDI data (e.g., ultrasound time of flight C-Scan data) for an affected structure may be mapped to a finite element model of a nominal of the structure (pristine, without inconsistency). A finite element method (FEM) based failure analysis on the reconstructed finite element model that contains the actual inconsistencies may then be carried out to indicate the extent of residual integrity of the structure.

Example implementations of the present disclosure may have any of a number of different contexts. One example of a suitable context is on incorporating delaminations caused by impact damage into the residual strength model. In this context, example implementations may provide an advanced algorithm to identify delamination areas between adjacent layers in a multi-layer structure, based on conventional ultrasound pulse echo data. Example implementations may reconstruct a finite element model of a nominal of the structure to contain the actual delaminations. FEM failure analysis (such as progressive failure analysis (PFA)) may be performed, so as to simulate the compression after impact (CAI) test to final failure, which may indicate the extent of residual integrity of the structure and thereby provide a more accurate assessment of the necessity of any needed rework (e.g., repair, replacement). Some example implementations may therefore enable real-time, condition-based structural damage assessment, rework and maintenance for composite aircraft fleets.

The present disclosure thus includes, without limitation, the following example implementations. In some example implementations, a method is provided for analyzing a structure. The method includes processing nondestructive inspection (NDI) data for an affected structure composed of a plurality of layers, with the NDI data being processed to define an area of inconsistency at an internal layer of the plurality of layers, or an interface between a particular pair of adjacent layers in the plurality of layers. The method includes receiving a finite element model of a nominal of the affected structure, with the finite element model being composed of a plurality of finite elements having respective element datasets, the plurality of finite elements including a mesh of finite elements for each of the plurality of layers, and finite elements at an interface between each pair of adjacent layers in the plurality of layers. The method also includes mapping the area of inconsistency to at least some of the plurality of finite elements that are thereby identified as affected finite elements, and that include finite elements of the mesh of finite elements for the internal layer, or the finite elements at the interface between the particular pair of adjacent layers. The method includes producing a reconstructed finite element model of the affected structure from the finite element model of the nominal, and a modified property or state value assigned to respective element datasets of the affected finite elements. The method includes performing a FEM failure analysis of the reconstructed finite element model under a load, with the FEM failure analysis producing an output that indicates an extent of residual integrity of the affected structure.

In some example implementations of the method of the preceding or any subsequent example implementation, or any combination thereof, the NDI data is processed to define a plurality of areas of inconsistency, at least two of which are at different layers of the plurality of layers, at interfaces between different pairs of adjacent layers in the plurality of layers, or at a layer of the plurality of layers and an interface between a pair of adjacent layers in the plurality of layers. In these example implementations, mapping the area of inconsistency includes mapping the plurality of areas of inconsistency that are thereby identified as the affected finite elements.

In some example implementations of the method of any preceding or any subsequent example implementation, or any combination thereof, the NDI data includes a plurality of data points having respective three-dimensional positions within a coordinate system of the affected structure. In these example implementations, processing the NDI data comprises converting data points of the plurality of data points to corresponding data points having respective two-dimensional positions at the internal layer or the interface between the particular pair of adjacent layers; and calculating an outer boundary of the corresponding data points to define the area of inconsistency at the internal layer or the interface between the particular pair of adjacent layers.

In some example implementations of the method of any preceding or any subsequent example implementation, or any combination thereof, processing the NDI data further includes assigning the modified property or state value to the area of inconsistency.

In some example implementations of the method of any preceding or any subsequent example implementation, or any combination thereof, the NDI data is processed to define a plurality of areas of inconsistency, at least two of which are at different layers of the plurality of layers, at interfaces between different pairs of adjacent layers in the plurality of layers, or at a layer of the plurality of layers and an interface between a pair of adjacent layers in the plurality of layers. In these example implementations, converting the data points and calculating the outer boundary are performed for each area of inconsistency of the plurality of areas of inconsistency.

In some example implementations of the method of any preceding or any subsequent example implementation, or any combination thereof, the NDI data includes a plurality of NDI datasets from a respective plurality of nondestructive inspections of the affected structure. In these example implementations, processing the NDI data comprises processing the plurality of NDI datasets to define a respective plurality of areas at the internal layer or interface between the particular pair of adjacent layers; and consolidating overlapping areas of the respective plurality of areas to define the area of inconsistency at the internal layer or interface between the particular pair of adjacent layers.

In some example implementations of the method of any preceding or any subsequent example implementation, or any combination thereof, mapping the area of inconsistency includes identifying each of the plurality of finite elements having at least a threshold percentage that overlaps the area of inconsistency.

In some example implementations, an apparatus is provided for implementation of a system for analyzing a structure. The apparatus comprises a processor and a memory storing executable instructions that, in response to execution by the processor, cause the apparatus to at least perform the method of any preceding example implementation, or any combination thereof. This may include implementation of subsystems of the system, such as a NDI process module, finite element model input interface, mapping module, reconstitution module and/or FEM failure analyzer, configured to perform steps of the method.

In some example implementations, a computer-readable storage medium is provided for analyzing a structure. The computer-readable storage medium is non-transitory and has computer-readable program code portions stored therein that, in response to execution by a processor, cause an apparatus to at least perform the method of any preceding example implementation, or any combination thereof.

These and other features, aspects, and advantages of the present disclosure will be apparent from a reading of the following detailed description together with the accompanying drawings, which are briefly described below. The present disclosure includes any combination of two, three, four or more features or elements set forth in this disclosure, regardless of whether such features or elements are expressly combined or otherwise recited in a specific example implementation described herein. This disclosure is intended to be read holistically such that any separable features or elements of the disclosure, in any of its aspects and example implementations, should be viewed as intended, namely to be combinable, unless the context of the disclosure clearly dictates otherwise.

It will therefore be appreciated that this Brief Summary is provided merely for purposes of summarizing some example implementations so as to provide a basic understanding of some aspects of the disclosure. Accordingly, it will be appreciated that the above described example implementations are merely examples and should not be construed to narrow the scope or spirit of the disclosure in any way. Other example implementations, aspects and advantages will become apparent from the following detailed description taken in conjunction with the accompanying drawings which illustrate, by way of example, the principles of some described example implementations.

BRIEF DESCRIPTION OF THE DRAWING(S)

Having thus described example implementations of the disclosure in general terms, reference will now be made to the accompanying drawings, which are not necessarily drawn to scale, and wherein:

FIGS. 3A, 3B and 3C illustrate the affected structure of FIG. 2, with nondestructive inspections from the topmost and bottommost layers, according to various example implementations;

DETAILED DESCRIPTION

Figure 1:
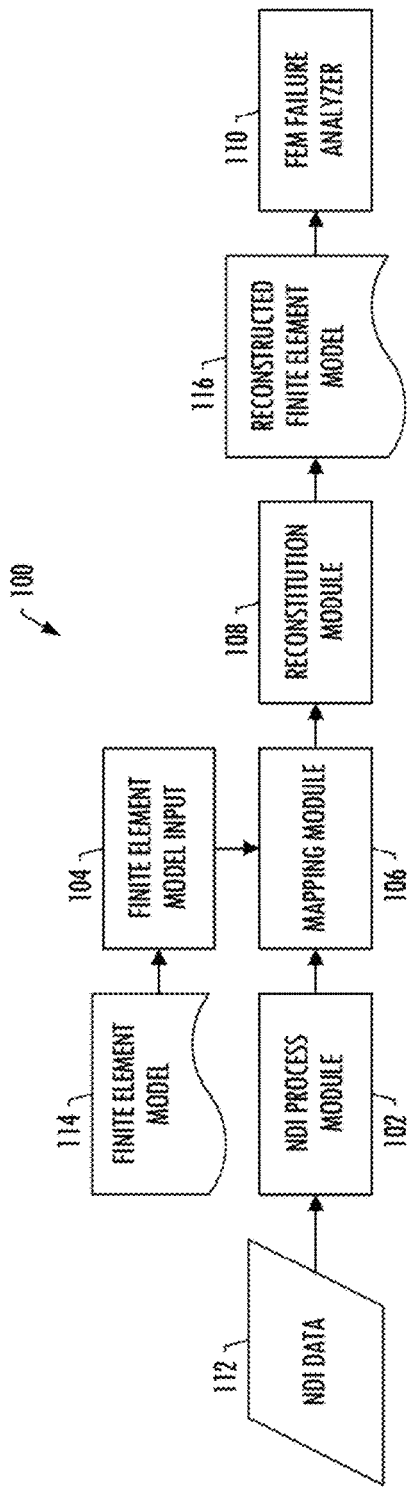
FIG. 1 illustrates a system for analyzing a structure, according to various example implementations of the present disclosure.

Some implementations of the present disclosure will now be described more fully hereinafter with reference to the accompanying drawings, in which some, but not all implementations of the disclosure are shown. Indeed, various implementations of the disclosure may be embodied in many different forms and should not be construed as limited to the implementations set forth herein; rather, these example implementations are provided so that this disclosure will be thorough and complete, and will fully convey the scope of the disclosure to those skilled in the art. For example, unless otherwise indicated, reference to something as being a first, second or the like should not be construed to imply a particular order. Also, for example, reference may be made herein to quantitative measures, values, relationships or the like (e.g., planar, coplanar, perpendicular). Unless otherwise stated, any one or more if not all of these may be absolute or approximate to account for acceptable variations that may occur, such as those due to engineering tolerances or the like. Like reference numerals refer to like elements throughout.

Example implementations of the present disclosure relate generally to structural finite element analysis and, in particular, to progressive failure analysis of a structure modeled with inconsistencies. FIG. 1 illustrates a system 100 for analyzing a structure, according to some example implementations of the present disclosure. The structure may be any of a number of different structures composed of one or more layers (more specifically "plies" in some examples), each of which in some examples may include fibers bound by a material often referred to as a matrix. Examples of suitable structures include composites, laminated composites and the like, such as laminated composites of unidirectional tape plies, layered metallic structures, metallic or composite skin and core (sandwich structures) and the like. These structures may be put to use in a number of different manners, such as on manned or unmanned vehicles (e.g., motor vehicles, railed vehicles, watercraft, aircraft, spacecraft).

The system 100 may include one or more of each of any of a number of different subsystems (each an individual system) for performing one or more functions or operations with respect to the structure analysis. As shown, for example, the system may include a nondestructive inspection (NDI) process module 102, a finite element model input interface 104, a mapping module 106, a reconstitution module 108 and a finite element method (FEM) failure analyzer 110 coupled to one another. Although being shown together as part of the system, it should be understood that any one or more of the NDI process module, finite element model input interface, mapping module, reconstitution module or FEM failure analyzer may function or operate as a separate system without regard to the other. And further, it should be understood that the system may include one or more additional or alternative subsystems than those shown in FIG. 1.

The NDI process module 102 may be configured to receive NDI data 112 (e.g., ultrasound C-Scan data) for an affected structure composed of a plurality of layers, which may be produced from a nondestructive inspection of the affected structure. The affected structure may be subjected to any of a number of different nondestructive inspection techniques that produce suitable NDI data. Examples of suitable techniques include ultrasound, magnetic-particle, liquid penetrant, radiographic, remote visual inspection (RVI), Fourier Transform Infrared Spectroscopy (FTIR), eddy-current testing, low coherence interferometry and the like. In the case of ultrasound, the inspection may produce C-Scan time of flight data, which may correspond to one example of suitable NDI data.

Figure 2:
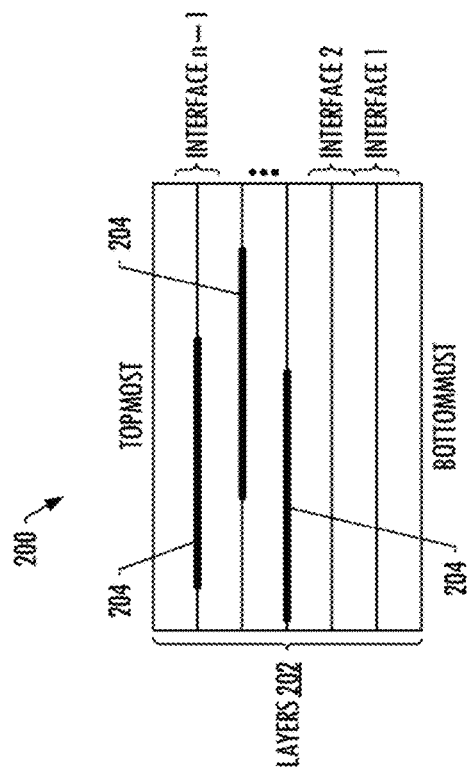
FIG. 2 illustrates an affected structure composed of a plurality of layers, and interfaces between adjacent layers in the plurality of layers, according to various example implementations.

FIG. 2 illustrates an affected structure 200 composed of a plurality of layers 202, and interfaces between adjacent layers in the plurality of layers. The structure may be composed of n layers, and correspondingly include n−1 interfaces between adjacent layers. The layers and interfaces may follow a number of different naming conventions, but in one example, may be numbered from a bottommost layer up to a topmost layer. As also shown, the affected structure includes a number of delaminations 204 at the interface between various adjacent layers.

Returning to FIG. 1, the NDI process module 102 may be configured to process the NDI data 112 to define an area of inconsistency at an internal layer of the plurality of layers, or an interface between a particular pair of adjacent layers in the plurality of layers. Inconsistency in the structure may manifest in any of a number of different manners. Examples of suitable types of inconsistencies include defects, inherent and induced damage, impact-induced delaminations and topology changes, heat-induced chemical changes and the like.

In some examples, the NDI data 112 may include a plurality of data points having respective three-dimensional (3D) positions (x, y, z) within a coordinate system of the affected structure. In these examples, the NDI process module 102 may be configured to convert data points of the plurality of data points to corresponding data points having respective two-dimensional (2D) positions (x, y) at the internal layer or the interface between the particular pair of adjacent layers (e.g., that reflect the z position). The NDI process module may then be configured to calculate an outer boundary (e.g., the convex hull) of the corresponding data points to determine the 2D boundary of and thereby define the area of inconsistency at the internal layer or the interface between the particular pair of adjacent layers. In some further examples, the NDI process module may be further configured to assign modified property or state values to specific areas of inconsistency.

In some examples, the NDI process module 102 may be configured to process the NDI data 112 to define a plurality of areas of inconsistency. These areas may be entirely at the same depth, entirely at different depths, or some at the same depth and others at different depths. Thus, in some examples, at least two areas of inconsistency may be at different depths. That is, in some examples, at least two of areas of inconsistency may be at different layers of the plurality of layers, at interfaces between different pairs of adjacent layers in the plurality of layers, or at a layer of the plurality of layers and an interface between a pair of adjacent layers in the plurality of layers. In these examples, the NDI process module may be configured to convert the data points and calculate the outer boundary for each area of inconsistency of the plurality of areas of inconsistency.

In some examples, the NDI data 112 includes a plurality of NDI datasets from a respective plurality of nondestructive inspections of the affected structure. In these examples, the NDI process module may be configured to process the plurality of NDI datasets to define a respective plurality of areas at the internal layer or interface between the particular pair of adjacent layers, and consolidate overlapping areas of the respective plurality of areas to define the area of inconsistency at the internal layer or interface between the particular pair of adjacent layers.

In accordance with a number of nondestructive inspection techniques, radiation or sound may be utilized to penetrate the structure and reflection or penetration of the radiation/sound may be used to distinguish between a defect (or other inconsistency) and the bulk of the structure. But in accordance with some of these techniques, the radiation/sound may not penetrate the first occurrence of a defect and therefore shadow or hide the detection of the defect/damage that is beyond the first occurrence. It may therefore be beneficial to perform a plurality of nondestructive inspections of the affected structure, such as from the topmost layer and the bottommost layer, which may facilitate identification of as many defects as possible.

FIG. 3A illustrates the affected structure 200 of FIG. 2, with nondestructive inspection using a transducer 302 emitting penetrating radiation/sound from the topmost layer, and the delaminations that may be identified therefrom. FIG. 3B illustrates the same affected structure, but with nondestructive inspection using the transducer emitting penetrating radiation/sound from the bottommost layer, and the delaminations that may be identified therefrom. FIG. 3C shows the delamination pattern that can be identified when the information from FIG. 3A and FIG. 3B is combined. In accordance with example implementations, NDI datasets from these inspections may be processed to define areas of inconsistency that for overlapping areas on any layer or interface may be consolidated to define the area for the layer/interface.

Returning to FIG. 1, the finite element model input interface 104 may be configured to receive a finite element model 114 of a nominal of the affected structure. The finite element model may be composed of a plurality of finite elements having respective element datasets. More particularly, the plurality of finite elements may include a mesh of finite elements for each of the plurality of layers, and finite elements at an interface between each pair of adjacent layers in the plurality of layers. That is, the finite element model of the structure may include one or more layers each of which is represented by a mesh of finite elements. In addition to the mesh of finite elements that represent each layer, the finite element model may include an inter-layer interface (finite) element between adjacent layers of each pair of adjacent layers in the plurality of layers. In some examples, each inter-layer interface element may be a zero-thickness finite element.

The finite elements of the finite element model may be or include one or more disjointed (non-overlapping) components in which each finite element may possess a set of distinguishing points called nodal points or nodes. In some example implementations, the nodal points may be located at the corners and/or end points of the elements such that the geometry of an element may be defined by the placement of geometric sets of nodal points.

The finite elements may also have respective element datasets including values of a property or state of the structure at the finite elements. Examples of suitable properties include geometric properties and constitutive properties such as residual thickness, principal curvature, elastic modulus, thermal coefficient of expansion and the like. The constitutive properties may specify the material behavior of the structure at the finite elements. Examples of suitable states include state variables such as components of the derived stress and strain tensors, and temperature at the finite elements.

The finite element model may be produced in any of a number of different manners, such as using commercially-available software tools. An example of a suitable software tool includes Abaqus, available from Dassault Systèmes S.A. of Vélizy-Villacoublay, France. Other examples of suitable software tools include Altair Hypermesh, available from Altair Engineering, Inc. of Troy, Mich.; PATRAN, available from MSC Software Corporation of Newport Beach, Calif.; the ANSYS software suite, available from ANSYS, Inc. of Canonsburg, Pa.; and the like.

The mapping module 106 may be configured to map the area of inconsistency to at least some of the plurality of finite elements—or otherwise associate the area of inconsistency with at least some of the plurality of finite elements—that are thereby identified as affected finite elements. These affected finite elements may include finite elements of the mesh of finite elements for the internal layer, or the finite elements at the interface between the particular pair of adjacent layers. In some examples, this may include the mapping module being configured to identify each of the plurality of finite elements having at least a threshold percentage that overlaps the area of inconsistency. And in some examples in which a plurality of areas of inconsistency including at least two at different depths is defined, the mapping module 106 may be configured to map the plurality of areas of inconsistency that are thereby identified as the affected finite elements.

Figure 4A:
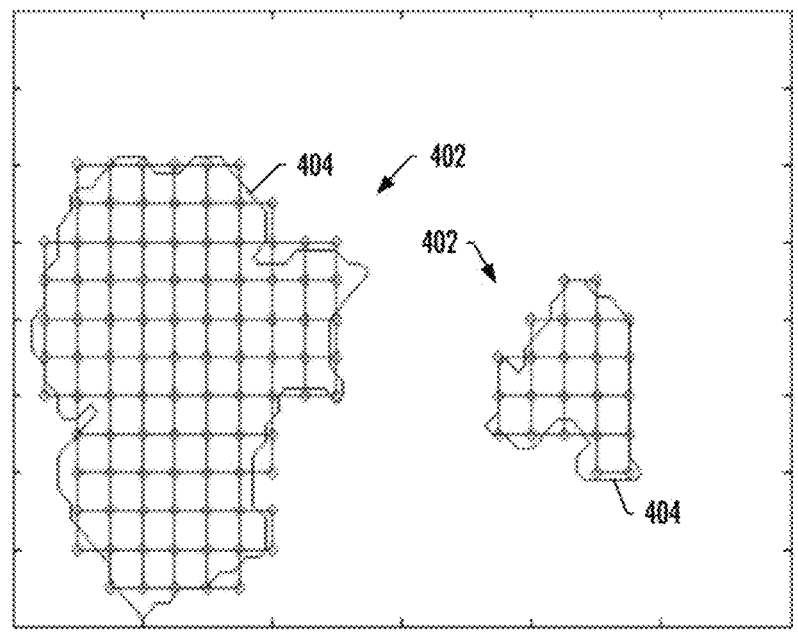
FIGS. 4A and 4B illustrate two areas of inconsistency mapped to finite elements at an interface between adjacent layers in a finite element model of an affected structure, according to various example implementations.
Figure 4B:
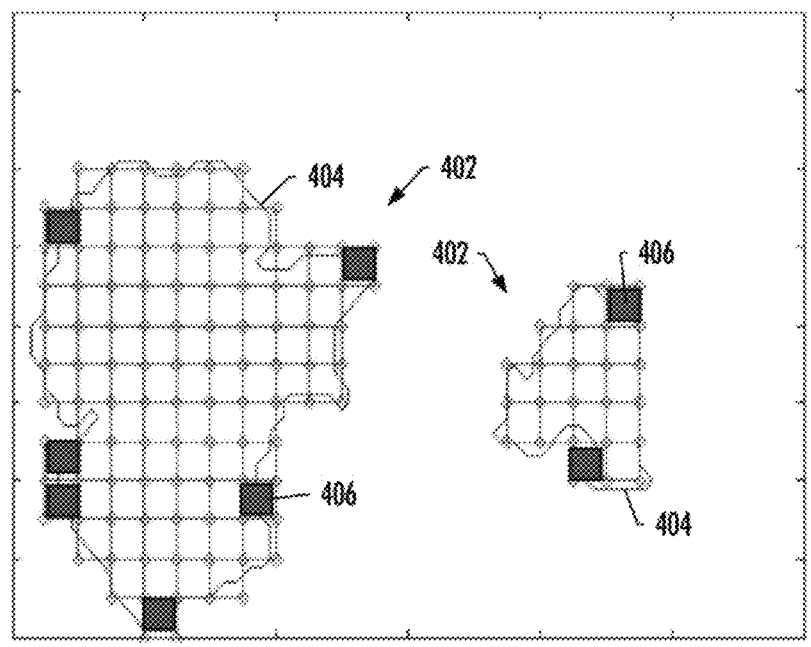

FIGS. 4A and 4B illustrate two areas of inconsistency 402 mapped to finite elements 404 (thereby identified as affected finite elements) at an interface between adjacent layers in a finite element model of an affected structure. In FIG. 4A, the affected finite elements may be those having at least 50% that overlaps an area of inconsistency; and in FIG. 4B, the affected finite elements may be those that instead have at least 40% that overlaps an area of inconsistency. As shown in FIG. 4B, reducing the threshold percentage from 50% to 40% may yield additional finite elements being identified as affected finite elements (two of eight additional finite elements are specifically designated with reference numeral 406 in FIG. 4B).

Returning again to FIG. 1, the reconstitution module 108 may be configured to produce a reconstructed finite element model 116 of the affected structure from the finite element model 114 of the nominal, and a modified property or state value assigned to respective element datasets of the affected finite elements. In some examples, a property value of the affected finite elements may be based on the NDI data and associated test data generated for the particular inconsistency. This data may be in the form of a look-up table that correlates the inconsistency and NDI data to the modified property value. For delaminations, for example, the affected finite elements may be assigned near-zero elastic properties and fracture energy values.

The FEM failure analyzer 110 may be configured to perform a FEM failure analysis of the reconstructed finite element model 116 under a load. In this regard, boundary conditions may be introduced to the reconstructed finite element model to apply a load to the model. This load may be any of a number of different types of loads depending on the particular analysis, but may include for example, tension, compression or the like. The FEM failure analysis may then be performed on the finite element model under the applied load. This FEM failure analysis may produce an output that indicates an extent of residual integrity of the affected structure.

The FEM failure analyzer 110 may be configured to perform any number of different FEM failure analyses of the reconstructed finite element model 116. In some examples, the layers and inter-layer interface elements may capture respectively potential layer and inter-layer failure modes. In these examples, the output of the FEM failure analysis may indicate the extent of any of the potential layer and inter-layer failure modes that result from the reconstructed finite element model under the load. These failure modes may be identified through any visualization tool that shows the extent of the failed elements within the reconstructed finite element model by probing an output variable that indicates whether an element has failed.

For its operations, the FEM failure analyzer 110 may include or otherwise benefit from commercially-available software tools. Examples of suitable tools include Abaqus; the ANSYS software suite (Fluent); NASTRAN/PATRAN, available from MSC Software Corporation; LS-DYNA®, available from Livermore Software Technology Corporation (LSTC) of Livermore, Calif.; and the like.

Figure 5:
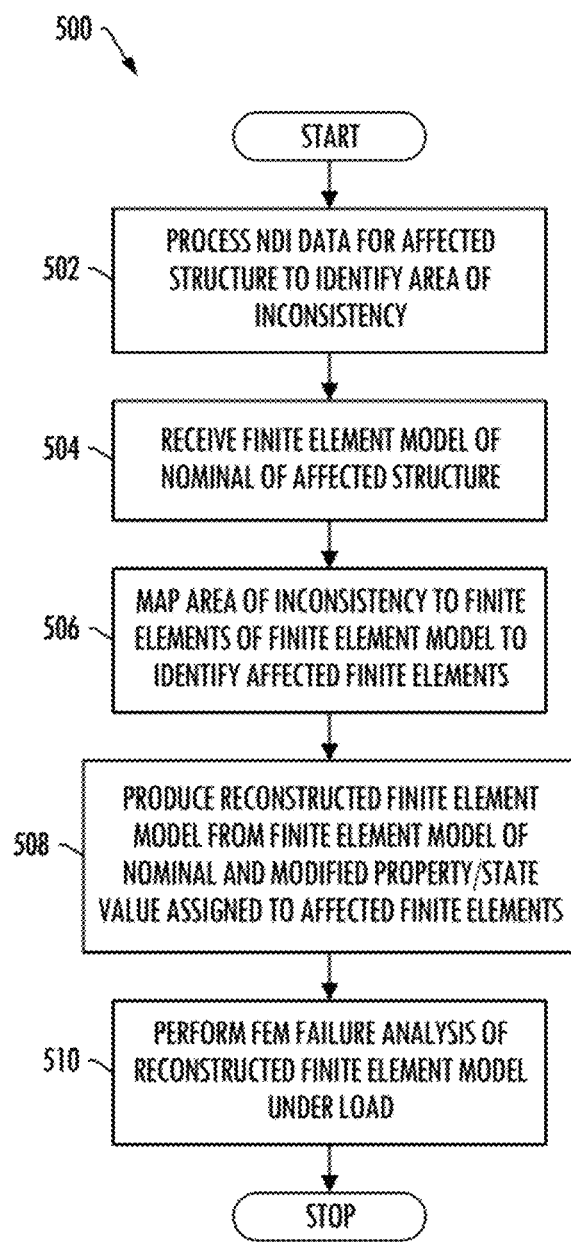
FIGS. 5, 6 and 7 are flowcharts illustrating various steps in methods according to various example implementations.

FIG. 5 is a flowchart illustrating various steps in a method 500 of analyzing a structure, according to some example implementations of the present disclosure. As shown at block 502, the method may include processing NDI data 112 for an affected structure composed of a plurality of layers, with the NDI data being processed to define an area of inconsistency at an internal layer of the plurality of layers, or an interface between a particular pair of adjacent layers in the plurality of layers.

The method may include receiving a finite element model 114 of a nominal of the affected structure, as shown at block 504. The finite element model may be composed of a plurality of finite elements having respective element datasets. The plurality of finite elements may include a mesh of finite elements for each of the plurality of layers, and finite elements at an interface between each pair of adjacent layers in the plurality of layers.

As shown at block 506, the method may also include mapping the area of inconsistency to at least some of the plurality of finite elements that are thereby identified as affected finite elements. These affected finite elements may include finite elements of the mesh of finite elements for the internal layer, or the finite elements at the interface between the particular pair of adjacent layers.

As shown at block 508, the method may include producing a reconstructed finite element model 116 of the affected structure from the finite element model 114 of the nominal, and a modified property or state value assigned to respective element datasets of the affected finite elements. And the method may include performing a FEM failure analysis of the reconstructed finite element model under a load, with the FEM failure analysis producing an output that indicates an extent of residual integrity of the affected structure, as shown at block 510. In instances in which the affected structure has insufficient residual integrity, the structure may be reworked (e.g., repaired, replaced); otherwise, the structure may be left intact without performing any rework.

Figure 6:
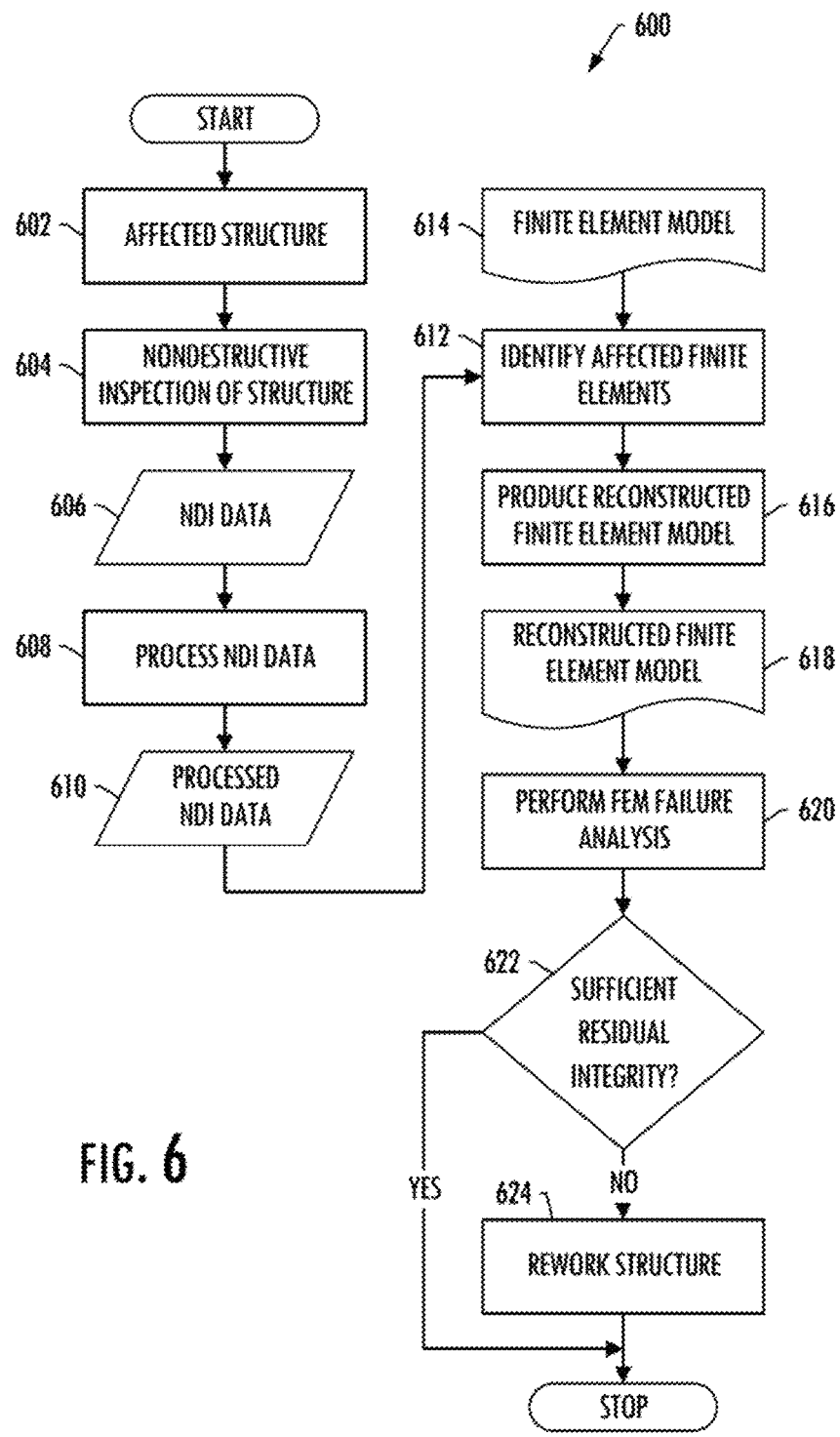

FIG. 6 is a flowchart illustrating more particularly various steps in a method 600 of analyzing a structure, which may be a more specific implementation of the method 500 of FIG. 5, according to some example implementations of the present disclosure. As shown at blocks 602 and 604, the method may include receipt and nondestructive inspection of an affected structure to produce NDI data 606 (e.g., NDI data 112). As shown at block 608, the method may include processing the NDI data to produce processed NDI data 610 in which an area of inconsistency may be defined at an internal layer of the plurality of layers, or an interface between a particular pair of adjacent layers in the plurality of layers.

As shown at block 612, the method may include receiving a finite element model 614 (e.g., finite element model 114) of a nominal of the affected structure, and mapping the area of inconsistency to at least some of its finite elements that are thereby identified as affected finite elements. The method may include reconstructing the finite element model of the affected structure from the nominal finite element model and a modified property or state value assigned to respective element datasets of the affected finite element, as shown at block 616, and thereby producing a reconstructed finite element model 618 (e.g., reconstructed finite element model 116).

The method may include performing a FEM failure analysis of the reconstructed finite element model 618 under a load, which may produce an output that indicates an extent of residual integrity of the affected structure, as shown at block 620. A determination may be made as to the sufficiency of the residual integrity of the affected structure, as shown at block 622. In instances in which the affected structure has insufficient residual integrity, the structure may be reworked (e.g., repaired, replaced), as shown at block 624.

Figure 7:
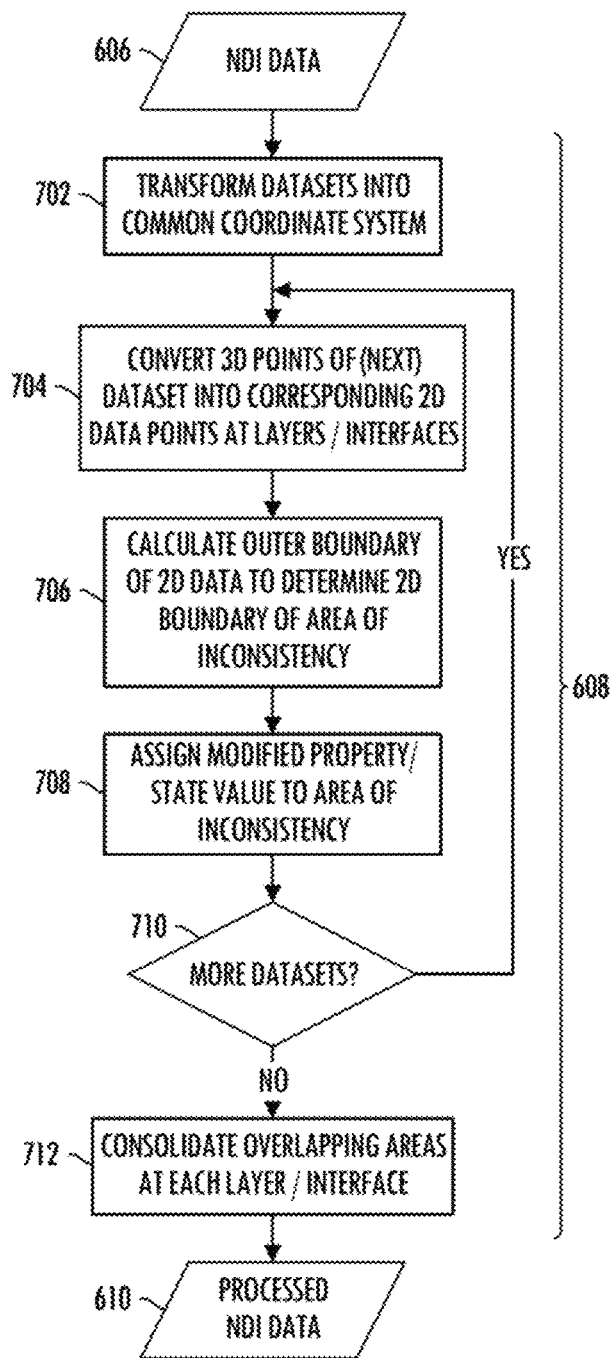

FIG. 7 illustrates various steps according to which NDI data 606 may be processed 608, according to some example implementations of the present disclosure. As shown at block 702, as appropriate, processing the NDI data may include transformation of any NDI dataset from nondestructive inspection of the affected structure, so that all NDI datasets are in a common coordinate system. As shown at block 704, data points of NDI data having respective 3D positions may be converted to corresponding data points having respective 2D positions at any appropriate layer (e.g., internal layer) or interface between the particular pair of adjacent layers. Then, as shown at block 706, the outer boundary of the corresponding data points may be calculated to determine the 2D boundary of and thereby define the area of inconsistency at the (internal) layer or the interface between the particular pair of adjacent layers. And as shown in block 708, a modified property or state value may be assigned to the area of inconsistency.

The above steps may repeat for other NDI datasets of the NDI data 606, which may reflect NDI datasets for respective nondestructive inspections of the affected structure, as shown at block 710. In some examples in which multiple overlapping areas of inconsistency are defined by the NDI datasets from multiple nondestructive inspections, the method may also include consolidation of overlapping areas, as shown at block 712. The process may then output the processed NDI data 610, which again may define an area of inconsistency at an internal layer of the plurality of layers, or an interface between a particular pair of adjacent layers in the plurality of layers.

According to example implementations of the present disclosure, the system 100 and its subsystems including the NDI process module 102, finite element model input interface 104, mapping module 106, reconstitution module 108 and/or FEM failure analyzer 110 may be implemented by various means. Means for implementing the system and its subsystems may include hardware, alone or under direction of one or more computer programs from a computer-readable storage medium. In some examples, one or more apparatuses may be configured to function as or otherwise implement the system and its subsystems shown and described herein. In examples involving more than one apparatus, the respective apparatuses may be connected to or otherwise in communication with one another in a number of different manners, such as directly or indirectly via a wired or wireless network or the like.

Figure 8:
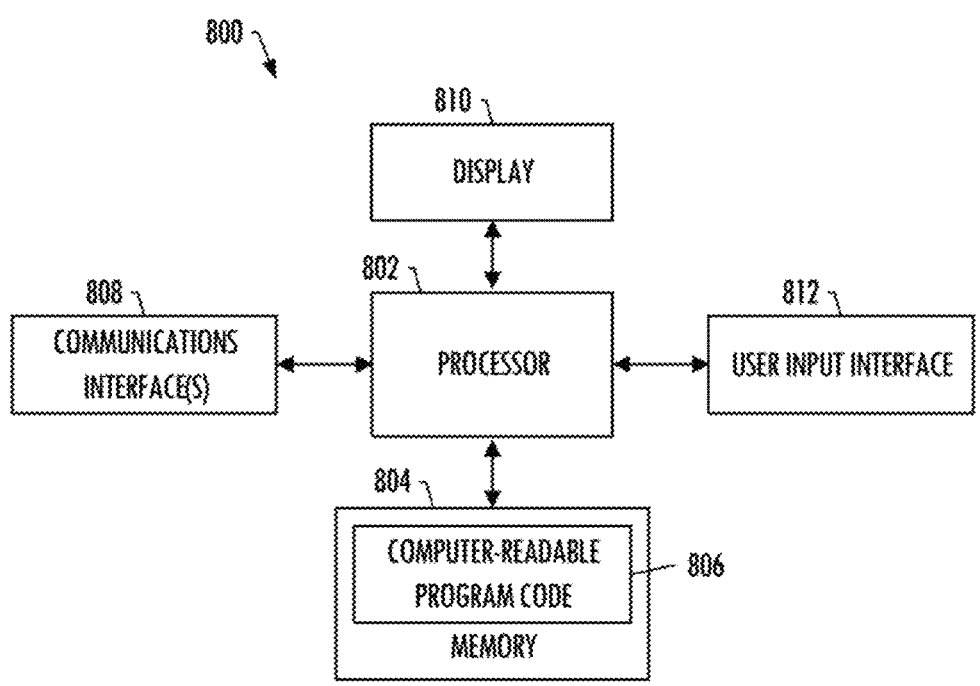
FIG. 8 illustrates an apparatus according to some example implementations.

FIG. 8 illustrates an apparatus 800 according to some example implementations of the present disclosure. Generally, an apparatus of exemplary implementations of the present disclosure may comprise, include or be embodied in one or more fixed or portable electronic devices. Examples of suitable electronic devices include a smartphone, tablet computer, laptop computer, desktop computer, workstation computer, server computer or the like. The apparatus may include one or more of each of a number of components such as, for example, a processor 802 (e.g., processor unit) connected to a memory 804 (e.g., storage device).

The processor 802 is generally any piece of computer hardware that is capable of processing information such as, for example, data, computer programs and/or other suitable electronic information. The processor is composed of a collection of electronic circuits some of which may be packaged as an integrated circuit or multiple interconnected integrated circuits (an integrated circuit at times more commonly referred to as a "chip"). The processor may be configured to execute computer programs, which may be stored onboard the processor or otherwise stored in the memory 804 (of the same or another apparatus).

The processor 802 may be a number of processors, a multi-core processor or some other type of processor, depending on the particular implementation. Further, the processor may be implemented using a number of heterogeneous processor systems in which a main processor is present with one or more secondary processors on a single chip. As another illustrative example, the processor may be a symmetric multi-processor system containing multiple processors of the same type. In yet another example, the processor may be embodied as or otherwise include one or more ASICs, FPGAs or the like. Thus, although the processor may be capable of executing a computer program to perform one or more functions, the processor of various examples may be capable of performing one or more functions without the aid of a computer program.

The memory 804 is generally any piece of computer hardware that is capable of storing information such as, for example, data, computer programs (e.g., computer-readable program code 806) and/or other suitable information either on a temporary basis and/or a permanent basis. The memory may include volatile and/or non-volatile memory, and may be fixed or removable. Examples of suitable memory include random access memory (RAM), read-only memory (ROM), a hard drive, a flash memory, a thumb drive, a removable computer diskette, an optical disk, a magnetic tape or some combination of the above. Optical disks may include compact disk-read only memory (CD-ROM), compact disk-read/write (CD-R/W), DVD or the like. In various instances, the memory may be referred to as a computer-readable storage medium. The computer-readable storage medium is a non-transitory device capable of storing information, and is distinguishable from computer-readable transmission media such as electronic transitory signals capable of carrying information from one location to another. Computer-readable medium as described herein may generally refer to a computer-readable storage medium or computer-readable transmission medium.

In addition to the memory 804, the processor 802 may also be connected to one or more interfaces for displaying, transmitting and/or receiving information. The interfaces may include a communications interface 808 (e.g., communications unit) and/or one or more user interfaces. The communications interface may be configured to transmit and/or receive information, such as to and/or from other apparatus(es), network(s) or the like. The communications interface may be configured to transmit and/or receive information by physical (wired) and/or wireless communications links. Examples of suitable communication interfaces include a network interface controller (NIC), wireless NIC (WNIC) or the like.

The user interfaces may include a display 810 and/or one or more user input interfaces 812 (e.g., input/output unit). The display may be configured to present or otherwise display information to a user, suitable examples of which include a liquid crystal display (LCD), light-emitting diode display (LED), plasma display panel (PDP) or the like. The user input interfaces may be wired or wireless, and may be configured to receive information from a user into the apparatus, such as for processing, storage and/or display. Suitable examples of user input interfaces include a microphone, image or video capture device, keyboard or keypad, joystick, touch-sensitive surface (separate from or integrated into a touchscreen), biometric sensor or the like. The user interfaces may further include one or more interfaces for communicating with peripherals such as printers, scanners or the like.

As indicated above, program code instructions may be stored in memory, and executed by a processor, to implement functions of the systems, subsystems, tools and their respective elements described herein. As will be appreciated, any suitable program code instructions may be loaded onto a computer or other programmable apparatus from a computer-readable storage medium to produce a particular machine, such that the particular machine becomes a means for implementing the functions specified herein. These program code instructions may also be stored in a computer-readable storage medium that can direct a computer, a processor or other programmable apparatus to function in a particular manner to thereby generate a particular machine or particular article of manufacture. The instructions stored in the computer-readable storage medium may produce an article of manufacture, where the article of manufacture becomes a means for implementing functions described herein. The program code instructions may be retrieved from a computer-readable storage medium and loaded into a computer, processor or other programmable apparatus to configure the computer, processor or other programmable apparatus to execute operations to be performed on or by the computer, processor or other programmable apparatus.

Retrieval, loading and execution of the program code instructions may be performed sequentially such that one instruction is retrieved, loaded and executed at a time. In some example implementations, retrieval, loading and/or execution may be performed in parallel such that multiple instructions are retrieved, loaded, and/or executed together. Execution of the program code instructions may produce a computer-implemented process such that the instructions executed by the computer, processor or other programmable apparatus provide operations for implementing functions described herein.

Execution of instructions by a processor, or storage of instructions in a computer-readable storage medium, supports combinations of operations for performing the specified functions. In this manner, an apparatus 800 may include a processor 802 and a computer-readable storage medium or memory 804 coupled to the processor, where the processor is configured to execute computer-readable program code 806 stored in the memory. It will also be understood that one or more functions, and combinations of functions, may be implemented by special purpose hardware-based computer systems and/or processors which perform the specified functions, or combinations of special purpose hardware and program code instructions.

Many modifications and other implementations of the disclosure set forth herein will come to mind to one skilled in the art to which the disclosure pertains having the benefit of the teachings presented in the foregoing description and the associated drawings. Therefore, it is to be understood that the disclosure is not to be limited to the specific implementations disclosed and that modifications and other implementations are intended to be included within the scope of the appended claims. Moreover, although the foregoing description and the associated drawings describe example implementations in the context of certain example combinations of elements and/or functions, it should be appreciated that different combinations of elements and/or functions may be provided by alternative implementations without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. An apparatus for implementation of a system for analyzing a structure including at least one inconsistency, the apparatus comprising a processor and a memory storing executable instructions that, in response to execution by the processor, cause the apparatus to implement at least:
- a nondestructive inspection (NDI) process module configured to process NDI data for the structure composed of a plurality of layers, the NDI data being processed to define an area of inconsistency at an internal layer of the plurality of layers, or an interface between a particular pair of adjacent layers in the plurality of layers;
- a finite element model input interface configured to receive a finite element model of the structure in which the structure does not include any inconsistency, the finite element model being composed of a plurality of finite elements having respective element datasets, the plurality of finite elements including a mesh of finite elements for each of the plurality of layers, and finite elements at an interface between each pair of adjacent layers in the plurality of layers;
- a mapping module configured to map the area of inconsistency to at least some of the plurality of finite elements that are thereby identified as affected finite elements, and that include finite elements of the mesh of finite elements for the internal layer, or the finite elements at the interface between the particular pair of adjacent layers;
- a reconstitution module configured to produce a reconstructed finite element model of the structure from the finite element model, and a modified property or state value assigned to respective element datasets of the affected finite elements; and
- a finite element method (FEM) failure analyzer configured to perform a FEM failure analysis of the reconstructed finite element model under a load, the FEM failure analysis producing an output that indicates an extent of residual integrity of the structure, wherein the NDI data includes a plurality of data points having respective three-dimensional positions within a coordinate system of the structure, and the NDI process module being configured to process the NDI data includes being configured to:

convert data points of the plurality of data points to corresponding data points having respective two-dimensional positions at the internal layer or the interface between the particular pair of adjacent layers; and calculate an outer boundary of the corresponding data points to determine the two-dimensional boundary of and thereby define the area of inconsistency at the internal layer or the interface between the particular pair of adjacent layers.

2. The apparatus of claim 1, wherein the NDI process module is configured to process the NDI data to define a plurality of areas of inconsistency, at least two of which are at different layers of the plurality of layers, at interfaces between different pairs of adjacent layers in the plurality of layers, or at a layer of the plurality of layers and an interface between a pair of adjacent layers in the plurality of layers, and wherein the mapping module being configured to map the area of inconsistency includes being configured to map the plurality of areas of inconsistency that are thereby identified as the affected finite elements.

3. The apparatus of claim 1, wherein the NDI process module being configured to process the NDI data further includes being configured to assign the modified property or state value to the area of inconsistency.

4. The apparatus of claim 1, wherein the NDI process module is configured to process the NDI data to define a plurality of areas of inconsistency, at least two of which are at different layers of the plurality of layers, at interfaces between different pairs of adjacent layers in the plurality of layers, or at a layer of the plurality of layers and an interface between a pair of adjacent layers in the plurality of layers, and wherein the NDI process module is configured to convert the data points and calculate the outer boundary for each area of inconsistency of the plurality of areas of inconsistency.

5. The apparatus of claim 1, wherein the NDI data includes a plurality of NDI datasets from a respective plurality of nondestructive inspections of the aeffed structure, and the NDI process module being configured to process the NDI data includes being configured to:

process the plurality of NDI datasets to define a respective plurality of areas at the internal layer or interface between the particular pair of adjacent layers; and consolidate overlapping areas of the respective plurality of areas to define the area of inconsistency at the internal layer or interface between the particular pair of adjacent layers.

6. The apparatus of claim 1, wherein the mapping module being configured to map the area of inconsistency includes being configured to identify each of the plurality of finite elements having at least a threshold percentage that overlaps the area of inconsistency.

7. A method of analyzing a structure including at least one inconsistency, the method comprising:

processing nondestructive inspection (NDI) data for the structure composed of a plurality of layers, the NDI data being processed to define an area of inconsistency at an internal layer of the plurality of layers, or an interface between a particular pair of adjacent layers in the plurality of layers;

receiving a finite element model of the structure in which the structure does not include any inconsistency, the finite element model being composed of a plurality of finite elements having respective element datasets, the plurality of finite elements including a mesh of finite elements for each of the plurality of layers, and finite elements at an interface between each pair of adjacent layers in the plurality of layers;

mapping the area of inconsistency to at least some of the plurality of finite elements that are thereby identified as affected finite elements, and that include finite elements of the mesh of finite elements for the internal layer, or the finite elements at the interface between the particular pair of adjacent layers;

producing a reconstructed finite element model of the structure from the finite element model, and a modified property or state value assigned to respective element datasets of the affected finite elements; and performing a finite element method (FEM) failure analysis of the reconstructed finite element model under a load, the FEM failure analysis producing an output that indicates an extent of residual integrity of the structure, wherein the NDI data includes a plurality of data points having respective three-dimensional positions within a coordinate system of the structure, and processing the NDI data comprises:

converting data points of the plurality of data points to corresponding data points having respective two-dimensional positions at the internal layer or the interface between the particular pair of adjacent layers; and calculating an outer boundary of the corresponding data points to determine the two-dimensional boundary of and thereby define the area of inconsistency at the internal layer or the interface between the particular pair of adjacent layers.

8. The method of claim 7, wherein the NDI data is processed to define a plurality of areas of inconsistency, at least two of which are at different layers of the plurality of layers, at interfaces between different pairs of adjacent layers in the plurality of layers, or at a layer of the plurality of layers and an interface between a pair of adjacent layers in the plurality of layers, and wherein mapping the area of inconsistency includes mapping the plurality of areas of inconsistency that are thereby identified as the affected finite elements.

9. The method of claim 7, wherein processing the NDI data further includes assigning the modified property or state value to the area of inconsistency.

10. The method of claim 7, wherein the NDI data is processed to define a plurality of areas of inconsistency, at least two of which are at different layers of the plurality of layers, at interfaces between different pairs of adjacent layers in the plurality of layers, or at a layer of the plurality of layers and an interface between a pair of adjacent layers in the plurality of layers, and wherein converting the data points and calculating the outer boundary are performed for each area of inconsistency of the plurality of areas of inconsistency.

11. The method of claim 7, wherein the NDI data includes a plurality of NDI datasets from a respective plurality of nondestructive inspections of the structure, and processing the NDI data comprises:

processing the plurality of NDI datasets to define a respective plurality of areas at the internal layer or interface between the particular pair of adjacent layers; and consolidating overlapping areas of the respective plurality of areas to define the area of inconsistency at the internal layer or interface between the particular pair of adjacent layers.

12. The method of claim 7, wherein mapping the area of inconsistency includes identifying each of the plurality of finite elements having at least a threshold percentage that overlaps the area of inconsistency.

13. A computer-readable storage medium for analyzing a structure including at least one inconsistency, the computer-readable storage medium being non-transitory and having computer-readable program code portions stored therein that in response to execution by a processor, cause an apparatus to at least:

process NDI data for the structure composed of a plurality of layers, the NDI data being processed to define an area of inconsistency at an internal layer of the plurality of layers, or an interface between a particular pair of adjacent layers in the plurality of layers;

receive a finite element model of the structure in which the structure does not include any inconsistency, the finite element model being composed of a plurality of finite elements having respective element datasets, the plurality of finite elements including a mesh of finite elements for each of the plurality of layers, and finite elements at an interface between each pair of adjacent layers in the plurality of layers;

map the area of inconsistency to at least some of the plurality of finite elements that are thereby identified as affected finite elements, and that include finite elements of the mesh of finite elements for the internal layer, or the finite elements at the interface between the particular pair of adjacent layers;

produce a reconstructed finite element model of the structure from the finite element model, and a modified property or state value assigned to respective element datasets of the affected finite elements; and perform a finite element method (FEM) failure analysis of the reconstructed finite element model under a load, the FEM failure analysis producing an output that indicates an extent of residual integrity of the structure, wherein the NDI data includes a plurality of data points having respective three-dimensional positions within a coordinate system of the structure, and the apparatus being caused to process the NDI data includes being caused to:

convert data points of the plurality of data points to corresponding data points having respective two-dimensional positions at the internal layer or the interface between the particular pair of adjacent layers; and calculate an outer boundary of the corresponding data points to determine the two-dimensional boundary of and thereby define the area of inconsistency at the internal layer or the interface between the particular pair of adjacent layers.

14. The computer-readable storage medium of claim 13, wherein the apparatus is caused to process the NDI data to define a plurality of areas of inconsistency, at least two of which are at different layers of the plurality of layers, at interfaces between different pairs of adjacent layers in the plurality of layers, or at a layer of the plurality of layers and an interface between a pair of adjacent layers in the plurality of layers, and wherein the apparatus being caused to map the area of inconsistency includes being caused to map the plurality of areas of inconsistency that are thereby identified as the affected finite elements.

15. The computer-readable storage medium of claim 13, wherein the apparatus being caused to process the NDI data further includes being caused to assign the modified property or state value to the area of inconsistency.

16. The computer-readable storage medium of claim 13, wherein the apparatus is caused to process the NDI data to define a plurality of areas of inconsistency, at least two of which are at different layers of the plurality of layers, at interfaces between different pairs of adjacent layers in the plurality of layers, or at a layer of the plurality of layers and an interface between a pair of adjacent layers in the plurality of layers, and wherein the apparatus is caused to convert the data points and calculate the outer boundary for each area of inconsistency of the plurality of areas of inconsistency.

17. The computer-readable storage medium of claim 13, wherein the NDI data includes a plurality of NDI datasets from a respective plurality of nondestructive inspections of the structure, and the apparatus being caused to process the NDI data includes being caused to:

process the plurality of NDI datasets to define a respective plurality of areas at the internal layer or interface between the particular pair of adjacent layers; and consolidate overlapping areas of the respective plurality of areas to define the area of inconsistency at the internal layer or interface between the particular pair of adjacent layers.

18. The computer-readable storage medium of claim 13, wherein the apparatus being caused to map the area of inconsistency includes being caused to identify each of the plurality of finite elements having at least a threshold percentage that overlaps the area of inconsistency.

* * * * *

UNITED STATES PATENT AND TRADEMARK OFFICE
CERTIFICATE OF CORRECTION

PATENT NO. : 10,502,719 B2
APPLICATION NO. : 14/832575
DATED : December 10, 2019
INVENTOR(S) : Hong Hue Tat et al.

Page 1 of 1

It is certified that error appears in the above-identified patent and that said Letters Patent is hereby corrected as shown below:

In the Claims

In Column 14, Claim 5, Line 13, "of the aeffed structure" should read -- of the structure --

Signed and Sealed this
Thirtieth Day of June, 2020

Andrei Iancu
*Director of the United States Patent and Trademark Office*